United States Patent [19]

Young

[11] 4,426,396

[45] Jan. 17, 1984

[54] PRESERVATION OF HARVESTED CROPS AND ANIMAL FEEDSTUFFS

[75] Inventor: Donald C. Young, Fullerton, Calif.

[73] Assignee: Union Oil Company of California, Los Angeles, Calif.

[21] Appl. No.: 272,687

[22] Filed: Jun. 11, 1981

[51] Int. Cl.$^3$ .............................................. A23K 3/00
[52] U.S. Cl. ........................................ 426/53; 71/30; 71/64.08; 71/64.1; 252/400 R; 424/166; 424/322; 426/69; 426/335; 426/532; 426/623; 426/630; 426/635; 426/636; 426/807
[58] Field of Search ..................... 426/52, 53, 69, 331, 426/335, 532, 623, 630, 635, 636, 654, 807; 424/78, 94, 166, 249, 322; 71/23, 30, 57, 29, 64.08, 64.10, 64.11; 252/400 R, 401, 405

[56] References Cited

U.S. PATENT DOCUMENTS

| | | | |
|---|---|---|---|
| 1,702,735 | 2/1929 | Legendre | 426/331 |
| 3,595,665 | 7/1971 | Huitson et al. | |
| 3,682,644 | 8/1972 | Nagakura | 426/69 X |
| 3,806,600 | 4/1974 | Lapore et al. | 424/317 |
| 3,873,728 | 3/1975 | Moore | 426/807 X |
| 3,899,588 | 8/1975 | Skov et al. | 424/317 |
| 4,006,265 | 2/1977 | Tamas et al. | 426/807 X |
| 4,033,747 | 7/1977 | Young | 71/30 |

FOREIGN PATENT DOCUMENTS

| | | | |
|---|---|---|---|
| 117171 | 1/1976 | German Democratic Rep. | |
| 145698 | 1/1981 | German Democratic Rep. | 426/623 |
| 1191470 | 5/1970 | United Kingdom | 426/69 |
| 1514835 | 6/1978 | United Kingdom | |

OTHER PUBLICATIONS

*Chemical Abstracts*, vol. 85, 45207u (1976).
Bothast et al., "Ammonia Kills Spoilage Molds in Corn", *Journal of Dairy Science*, vol. 56, pp. 241–245 (1973).
Bothast et al., "Preservation of High-Moisture Corn: A Microbiological Evaluation", *Journal of Dairy Science*, vol. 58, pp. 386–391 (1975).

*Primary Examiner*—Arthur L. Corbin
*Attorney, Agent, or Firm*—Dean Sandford; Gregory F. Wirzbicki; Robert A. Franks

[57] ABSTRACT

The growth of microorganisms in stored crops, and especially in animal feedstuffs, is inhibited by the application, in the presence of urease, of a preservative composition which comprises ammonia, urea and urea polymers in a fluid medium. Urea polymers which are useful include biuret, triuret, cyanuric acid, urea cyanurate and other compounds which decompose to form ammonia. The effect of treatment with the preservative composition is to provide an immediate microorganism-inhibiting ammonia level, which, due to delayed decomposition of the urea and urea polymers, is sustained to some significant degree during prolonged storage of the treated material.

18 Claims, No Drawings

PRESERVATION OF HARVESTED CROPS AND ANIMAL FEEDSTUFFS

BACKGROUND OF THE INVENTION

1. Field of the Invention

This invention relates to the preservation of stored crops including animal feedstuffs, and more particularly to the storage of such materials by treating the material to be stored with a slow release microorganism growth-inhibiting composition.

2. Description of the Present Art

The growth of microorganisms causes serious problems in the storage of grains and forages. In past years, a primary method for preserving such stored materials has been the reduction of moisture content to a level below about 13 percent by weight. This was formerly accomplished by permitting the mature plants to dry naturally in the field before harvesting, but more commonly now involves artificial drying procedures which remove moisture after harvesting.

Artificial drying procedures have encouraged earlier harvesting, which minimize exposure to field losses from adverse weather conditions. In addition, excessive field drying is not desirable for cereal grains which are to be harvested by modern mechanical devices, since serious losses due to separation of the kernels from the stalk are more likely to result. However, the continually increasing costs of fuel materials, which must be burned to effect the drying of harvested plants, have had a severe impact upon the economics of agricultural operations.

Spoilage of stored feedstuffs is primarily caused by pathogenic microorganisms, many of which are classified as molds. Lapore et al., in U.S. Pat. No. 3,806,600, have identified some of the offensive molds as *Sclerotium rolfsii, Rhizoctionia solani*, Fusarium, Pythium, Penicillium, and Aspergillus species. Molds and fungi are well known to produce poisons (mycotoxins), causing sicknesses and even deaths among animals ingesting feedstuffs which carry the mold or fungus.

A variety of treatments have been proposed or used to control mold growth on high-moisture (over 13 percent by weight) grains and forage. Huitson et al. show the use of acetic acid, formic acid or binary and ternary mixtures of acetic, propionic and formic acids as mold growth-inhibitors for crops and animal feedstuffs in U.S. Pat. No. 3,595,665. In U.S. Pat. No. 3,806,600, Lapore et al. describe the use of ammonium and potassium isobutyrates to inhibit the growth of organisms. U.S. Pat. No. 3,899,588 to Skov et al. is directed to a composition for preserving silage or seeds, comprising an aqueous solution of the product from ammoniating an alkanoic acid having 2 to 10 carbon atoms. A comparison of the effectiveness of sodium chloride, sodium propionate, propionic acid, a mixture of acetic and propionic acids, and ammonium isobutyrate was reported by H. K. Goering and C. H. Gordon in *Journal of Dairy Science*, Vol. 56, No. 10 at pages 1346–1351 (1973).

R. J. Bothast et al., in *Journal of Dairy Science*, Vol. 56, No. 2, at pages 241–245 (1973) demonstrate the elimination of molds and yeasts from corn which contained 26 percent moisture by treating the corn with 2 percent (based upon dry weight) of ammonia. A subsequent paper by Bothast et al. in *Journal of Dairy Science*, Vol. 58, No. 3, pages 386–391 (1975) compared the performance of ammonia, ammonium isobutyrate, isobutyric acid, and propionic-acetic acid in the preservation of freshly harvested, 27 percent moisture corn, stored in bins.

Ammonia and propionic acid solutions were also tested and compared as preservatives by Vandegraft et al., as reported in *Cereal Chemistry*, Vol. 52, pages 79–84 (1975).

East German Patent 117,171, as abstracted in *Chemical Abstracts*, Vol. 85, 45207$\mu$ (1976), discloses the use of urea as a preservative for high-moisture grain to be used for feed, attributing the preservative effect to the generation of ammonia through hydrolysis of the urea.

In United Kingdom Pat. No. 1,514,835, the treatment of grass silage with mixtures of urea and propionic acid is described. Treatment with the mixtures was found to yield a better stored product that if only a urea treatment was used.

Several other chemical treatments have been utilized for preserving animal feedstuffs during storage, including aldehydes, sulfur, metal salts, guanidine and others, but without notable success. A need remains for an inexpensive preservation treatment which is easily applied to undried crop materials prior to storage, and which remains effective during the entire storage period, even though the exact storage duration is normally not known when a treatment is applied.

Accordingly, it is an object of the present invention to provide a treatment for inhibiting the growth of harmful microorganisms during the storage of crop materials.

Another object of the invention is to provide a treatment which is relatively inexpensive, and can be safely applied by an unskilled worker.

It is a further object to provide a treatment which remains effective over prolonged periods of storage, but which will not adversely affect the usefulness of treated materials if storage is unexpectedly shortened.

These and other objects will appear more clearly from consideration of the following description and examples.

SUMMARY OF THE INVENTION

The invention is directed to a composition for treating crops, especially animal feedstuffs, destined for storage so as to inhibit the growth of microorganisms, particularly molds, which eventually render the stored material unfit for its intended purpose. This composition is comprised of ammonia, urea, and urea polymers, preferably in an aqueous solution. The urea polymers, as referenced herein, are hereby defined as materials which decompose, in an environment such as that of stored crop materials, to form ammonia as a product, including, without limitation, biuret, triuret, cyanuric acid, urea cyanurate and other materials. Optionally, the composition can also contain the enzyme urease.

When the composition of this invention is applied to stored crops, the ammonia component immediately acts to reduce bacterial content and kill internal and external fungi (molds and yeasts). This ammonia, however, is volatile and rather easily dissipated from the storage bins, after which urea hydrolysis supplies additional ammonia to maintain the fungicidal activity. The slower-decomposing urea polymers act to sustain the presence of ammonia for a period of time beyond decomposition of the initially present urea. In this manner, the composition can be used to protect crops during prolonged periods of storage.

DESCRIPTION OF THE INVENTION

The composition of this invention, for preserving stored crops against the growth of microorganisms, comprises ammonia, urea, and urea polymers in a fluid medium. Optionally, the enzyme urease can be added.

This invention is useful for the preservation of diverse crop materials, including grains such as barley, oats, corn, wheat, rye, maize, soybeans, sorghum, sunflower seeds, rape seed and the like, and other materials which are utilized primarily as animal feedstuffs, such as silage, including hays and alfalfa. The invention is also useful for preserving processed crop materials, an example being grain mash resulting from the fermentation and distillation of alcohol. The mash is very wet, but possesses substantial feed values for cattle and other agricultural animals. Such processed matter is included within the general definition of "crop materials". Mixed crop materials can also be preserved, as exemplified by the use of the invention for mixed animal feeds.

Components of the preservation composition are well known to the agricultural chemical industry, and are readily available from a large number of suppliers to that industry. Ammonia can be utilized either in its anhydrous form or dissolved in water as aqua ammonia. Urea is typically marketed as the solid compound (crystalline, granulated or prilled) or in aqueous solutions, which can also contain ammonia.

Urea polymers which are useful include, without limitation, biuret, triuret, cyanuric acid, urea cyanurate and other compounds which form ammonia upon decomposition in an environment such as that involved in the storage of crop materials. An additional requirement is that the urea polymers be readily dispersible, and preferably soluble, in the dispersions or solutions of ammonia and urea which comprise the composition of this invention. A particular composition can contain a single urea polymer or a mixture of urea polymers, depending upon the desired ammonia release program.

Control of the microorganism growth is due to the presence of ammonia in the preservative composition. An ammonia level of 0.5 percent of the dry weight has been established as one which rapidly kills molds and yeasts in corn and prevents the proliferation of bacteria [see Bothast et al., *Journal of Dairy Science*, Vol. 56, pages 241–245 (1975)]. Bothast et al. have also reported that a 2 percent level of ammonia acts to reduce bacteria levels. The initial action of ammonia is apparently very rapid; molds and yeasts are eliminated from treated materials within a few hours following application. It is preferred, therefore, to provide sufficient ammonia in the composition so that a minimum of about 0.5 percent by weight ammonia is present on the treated material, even though lower levels, e.g., about 0.1 percent by weight can be used with possibly less rapid effect.

The actual ammonia concentration will be determined from such factors as its solubility or miscibility in a particular preservative composition, the nature of composition storage and application equipment which is available, the rate at which composition is to be applied to the crop, etc., but usually will be up to about 20 percent by weight in the composition.

The ammonia treatment, however, can only be considered as a temporary measure. Ammonia concentrations will be reduced due to diffusion losses from the storage enclosure, since ammonia is quite volatile and storage is normally not in a gastight enclosure. In addition, some ammonia is absorbed, over a period of time, into the interior of the stored material, thereby rendering the ammonia ineffective for microbial control. The well-known phenomenon of microbiological nitorgen fixation also acts to reduce ammonia levels by chemical conversion.

Urea is utilized in the preservative composition to provide replacement ammonia as the original amount is depleted. Through the catalytic action of the enzyme urease, urea is hydrolyzed to ammonia and carbon dioxide. Urease is highly specific in its operation, catalyzing only the hydrolysis of urea. Since the enzyme is present to some extent in practically all farm crops, all urea which is added by means of this invention would be very rapidly hydrolyzed, except for the inhibiting effect of ammonia upon the activity of urease. It has been found that high levels of ammonia completely stop urease-catalyzed urea hydrolysis, but that the hydrolysis reaction is re-established at low ammonia concentrations. In a fairly well closed system, as in crop material storage, this phenomenon can be used to supply a useful ammonia level over a considerable period.

The concentration of urea to be used depends, inter alia, upon the ammonia leakage rate from the storage enclosure and the expected total length of storage for treated material, so is not a readily defined quantity. It has been found useful, however, to provide urea in the preservative composition at approximately two to ten times the ammonia concentration used. This level should be adequate for many storage situations.

Even though urease is almost ubiquitous, it will occasionally be necessary to include the enzyme in a preservative composition. This will be the case, for example, if an already stored material was fumigated prior to storage, thereby destroying the originally present urease, and it is subsequently desired to remove the material to a new storage location. Also, some crops contain much less urease than others, and additions to the preservative composition will insure that an effective amount is present during storage. Due to the low cost of urease, and the minor quantity which is needed, even its routine addition to all preservative solutions will not have a large effect upon the economics of the treatment. When urease is used in a composition, it should be present in an amount above about 0.05 percent of the ammonia concentration. A level of urease which is about 0.5 percent of the ammonia concentration should be sufficient for the storage of most crops using this invention up to a maximum level of about 0.5 percent by weight in the composition.

In addition to the aforementioned components, it is advisable to add at least one urea polymer to a preservative composition, for instances in which the possibility of very long term storage of crops exists. These polymers, described in previous paragraphs, slowly decompose by chemical reactions (primarily hydrolysis) to form ammonia. Biuret, for example, hydrolyzes to ammonia and urea, while triuret forms ammonia and biuret upon hydrolysis. Hydrolysis of urea polymers generally proceeds quite slowly and has a rate which is somewhat temperature dependent. There is not an enzyme catalyst available to assist in these reactions, although one report has suggested the possibility of an enzyme which is specific for triuret hydrolysis [*Chemical Abstracts*, Vol. 85, 59295h (1976)].

When a urea polymer is provided, it is desirable to establish its concentration at a level up to about the same as the concentration of ammonia in the composition.

The components of the composition are preferably combined in the form of an aqueous solution, except for formulations wherein slightly soluble or insoluble urea polymers are present, in which case an aqueous dispersion is formed. The invention, however, is not restricted to aqueous media, since a number of nonaqueous fluids also can be used including, without limitation, alcohols, sorbitols, vegetable oils and sugar-containing substances such as molasses (which, although normally containing water, will, for purposes of this invention, be considered as nonaqeous). Alcohols and sorbitols are able to dissolve substantial amounts of the preservative compounds of this invention, forming solutions and dispersions similar to those previously described as aqueous. Vegetable oils, sugar-containing substances and the like, typically do not dissolve many of the preservative compounds to a great extent, so will form dispersions. If a particular user of the composition does not have equipment suitable for handling dispersions, a more soluble urea polymer should be chosen and concentrations of all components should be adjusted so that a solution will be maintained at the anticipated ambient temperature conditions.

A preservative composition of this invention can be applied by method, known to those skilled in the art, for applying coatings of other preservatives for stored crops. In many instances, material to be stored will be raised by means of a conveyor or auger and introduced into the top of a storage enclosure. The preservative can be easily applied through one or more spary nozzles situated at any location along a conveyor or auger. It is also possible to siturate spray nozzles immediately below the discharge point of a conveyor or auger to coat material as it falls into the storage enclosure.

The dispersing spray nozzles will typically be connected to a pump, and a means for measuring and controlling the flow rate of preservative will be provided. This uncomplicated equipment requirement facilitates the use of the invention by lesser skilled workers at a minimized expense.

As an additional benefit, the compositions of this invention can be safely handled by relatively untrained individuals; the only required safety precautions are those incident to the handling of ammonia solutions, common commodities in a farm environment.

The compositions of this invention can be safely used even in instances where the storage duration is not capable of prediction. For long-term storage, diffusion and other processes will effectively reduce the concentrations of the chemical agents applied to the crop material. However, even if storage duration is unexpectedly shortened, the preservative composition components can be chosen from those permitted by regulatory agencies in animal feeds. For example, a preservative dispersion of ammonia, urea, and biuret in molasses or vegetable oil would be acceptable under current regulations for use in animal feeds, as would an aqueous solution of ammonia, urea and biuret. Several other compositions could also be used. Indeed, several of the components are currently utilized as animal feed supplements.

Further description of the invention is provided by means of the following example, which is only for purposes of illustration and should not be construed as limiting the invention defined in the appended claims. In the example, all percentage compositions are expressed on a weight basis.

EXAMPLE

An experiment is performed to compare the effectiveness of compositions according to this invention with that of an aqueous ammonia solution. Four aqueous solutions are prepared for testing, formulated as in Table I.

TABLE I

| Number | Composition; Percent | | | | Total $NH_3$ Percent | $NH_3$ Release Percent | | |
|---|---|---|---|---|---|---|---|---|
| | Ammonia | Urea | Biuret | Urease | | Rapid | Slow | Very Slow |
| 1 | 0 | 40 | 0 | 0.05 | 21 | 0 | 21 | 0 |
| 2 | 10 | 40 | 2 | 0.05 | 31 | 6 | 23 | 2 |
| 3 | 10 | 40 | 0 | 0.05 | 30 | 6 | 24 | 0 |
| 4 | 30 | 0 | 0 | 0 | 30 | 30 | 0 | 0 |

Duplicate 300 gram portions of yellow dent maize, having microbial counts of $8.50 \times 10^4$ molds per gram, $2.9 \times 10^6$ bacteria per gram, and a 25 percent moisture content, are placed in 1000 milliliter Erlenmeyer flasks, and the flasks are connected to a source of humidified air, supplied at a rate of 10 milliliters per minute. Each flask is provided with sufficient solution (from Table I) to provide a 0.2 percent total ammonia level in the maize. Two control portions are also provided, one of which is not aerated. At the onset of visible microbial growth, the flasks are emptied and the contents analyzed for microbial counts. Results are shown in Table II.

TABLE II

| Treatment | Elapsed Time to Microbial Growth, Days | Microbial Count, per gram | |
|---|---|---|---|
| | | Molds | Bacteria |
| None, no air | 5 | $5.00 \times 10^5$ | $1.73 \times 10^7$ |
| None, aerated | 3 | $1.50 \times 10^7$ | $3.33 \times 10^7$ |
| Solution 1 | 3 | $1.40 \times 10^7$ | $1.16 \times 10^8$ |
| Solution 2 | 5 | $1.78 \times 10^6$ | $2.02 \times 10^8$ |
| Solution 3 | 5 | $2.40 \times 10^6$ | $2.91 \times 10^8$ |
| Solution 4 | 15 | $1.30 \times 10^5$ | $4.43 \times 10^8$ |

These results indicate that an initial ammonia concentration is needed for a composition to be effective as a preservative.

The experiment is repeated at a higher treatment level (0.8 percent total ammonia in the maize) to compare the storage times obtainable with three of the solutions. When visible microbial growth appears, microbial counts are performed, with the results as in Table III.

TABLE III

| Treatment | Elapsed Time to Microbial Growth, Days | Microbial Count, per gram | |
|---|---|---|---|
| | | Molds | Bacteria |
| Solution 2 | 96 | 0 | $1.83 \times 10^4$ |
| Solution 3 | 96 | 0 | $1.87 \times 10^5$ |
| Solution 4 | 39 | $1.33 \times 10^7$ | $1.34 \times 10^8$ |

According to these results, the slow release compositions are much more effective than an ammonia solution in promoting long-term storage. Also significant is the showing that the urea and urea polymer compositions continue to be effective against mold growth at the termination of storage, and that the solution containing a urea polymer provides greater control of bacterial growth.

It should be noted that the test conditions tend to accelerate microbial proliferation over that which would be expected in the typical commercial storage (due to the relatively high air flow which is maintained during the test), and that the experimental results are primarily useful for comparative purposes. Under normal storage conditions, the use of this invention would provide many months of storage without loss due to microbial growth.

Various embodiments and modifications of this invention have been described in the foregoing example and description, and further modification will be apparent to those skilled in the art. Such modifications are included within the scope of the invention as defined by the following claims.

I claim:

1. The method for preserving harvested crops and animal feedstuffs which comprises applying, in the presence of urease, a preservative composition comprising ammonia and urea in a fluid medium to said crops in an amount effective to prevent the growth of pathogenic microorganisms.

2. The method defined in claim 1 wherein the composition further includes one or more urea polymers.

3. The method defined in claim 2 wherein said urea polymers are selected from the group consisting of biuret, triuret, cyanuric acid and urea cyanurate.

4. The method defined in claim 2 wherein said urea polymers are present in an amount up to about the ammonia concentration of the composition.

5. The method defined in claim 1 wherein the composition is in the form of a solution.

6. The method defined in claim 1 wherein the composition is in the form of a dispersion.

7. The method defined in claim 1 wherein the fluid medium is nonaqueous.

8. The method defined in claim 1 wherein the fluid medium is aqueous.

9. The method defined in claim 1 wherein the composition comprises an aqueous solution of: (a) ammonia, in an amount up to about fifteen percent by weight; and (b) urea, in an amount at least about twice the ammonia concentration, up to about forty percent by weight.

10. The method defined in claim 1 wherein the urease is present in the composition.

11. The method defined in claim 10 wherein the composition comprises up to about 0.5 percent by weight urease.

12. The method defined in claim 1 wherein sufficient composition is used to provide at least about 0.2 percent by weight of total ammonia in the harvested crops.

13. The method for preserving harvested crops and animal feedstuffs which comprises applying, in the presence of urease, a preservative composition, comprising: (a) ammonia, in an amount up to about fifteen percent by weight; (b) urea, in an amount at least about twice the ammonia concentration, up to about forty percent by weight; and (c) one or more urea polymers selected from the group consisting of biuret, triuret, cyanuric acid and urea cyanurate in an amount up to about the ammonia concentration, in a fluid medium to said crops, in an amount effective to prevent the growth of pathogenic microorganisms.

14. The method defined in claim 13 wherein the urease is present in the composition, in an amount up to about 0.5 percent by weight.

15. The method defined in claim 13 wherein sufficient composition is applied to the crops to provide at least about 0.2 percent by weight of total ammonia in the harvested crops.

16. Harvested crops which have been treated by the method defined in claim 13.

17. The method for preserving harvested crops and animal feedstuffs which comprises applying to said crops a preservative composition comprising an aqueous solution of: (a) ammonia, in an amount up to about fifteen percent by weight; (b) urea, in an amount at least about twice the ammonia concentration, up to about forty percent by weight; (c) biuret, in an amount up to about two percent by weight; and (d) urease, in an amount up to about 0.5 percent by weight, said composition being applied in an amount sufficient to provide at least about 0.2 percent by weight of total ammonia in the harvested crops.

18. Harvested crops which have been treated by the method defined in claim 17.

* * * * *